(12) United States Patent
Van Halsema

(10) Patent No.: US 7,927,487 B2
(45) Date of Patent: Apr. 19, 2011

(54) CHROMATOGRAPHIC COLUMN SYSTEM

(75) Inventor: Frans Emo Diderik Van Halsema, Veenendaal (NL)

(73) Assignee: Cooperatie AVEBE U.A., Veendam (NL)

( * ) Notice: Subject to any disclaimer, the term of this patent is extended or adjusted under 35 U.S.C. 154(b) by 15 days.

(21) Appl. No.: 12/532,350

(22) PCT Filed: Mar. 25, 2008

(86) PCT No.: PCT/NL2008/050170
§ 371 (c)(1),
(2), (4) Date: Sep. 21, 2009

(87) PCT Pub. No.: WO2008/118016
PCT Pub. Date: Oct. 2, 2008

(65) Prior Publication Data
US 2010/0116723 A1    May 13, 2010

(30) Foreign Application Priority Data

Mar. 23, 2007  (EP) ..................................... 07104785

(51) Int. Cl.
*B01D 15/08* (2006.01)
(52) U.S. Cl. ..................................... 210/198.2; 210/656
(58) Field of Classification Search .................. 210/635, 210/656, 659, 198.2, 502.1
See application file for complete search history.

(56) References Cited

U.S. PATENT DOCUMENTS

| 4,249,828 | A | * | 2/1981 | Condolios ..................... 366/102 |
| 4,549,812 | A |   | 10/1985 | Bothorel et al. |
| 5,036,212 | A |   | 7/1991 | Staudinger |
| 5,759,395 | A |   | 6/1998 | Hagerlid |
| 6,027,650 | A | * | 2/2000 | Van Reis et al. ............... 210/656 |
| 6,620,326 | B1 | * | 9/2003 | Lihme et al. ................... 210/635 |
| 2006/0266684 | A1 | * | 11/2006 | Pichl .......................... 210/198.2 |

FOREIGN PATENT DOCUMENTS

| DE | 2513001 | 10/2007 |
| EP | 1420164 A2 | 5/2004 |
| GB | 2204949 A1 | 11/1988 |
| WO | 9524760 | 9/1995 |
| WO | 9965586 | 12/1999 |
| WO | 0205923 A1 | 1/2002 |
| WO | 03060433 A2 | 7/2003 |
| WO | 2006069797 A1 | 7/2006 |

* cited by examiner

*Primary Examiner* — Ernest G Therkorn
(74) *Attorney, Agent, or Firm* — Hoffman & Baron, LLP

(57) ABSTRACT

Chromatographic column system, in particular a chromatographic column system of the expanded bed adsorption column type comprises a column connected to a fluid inlet and a fluid outlet and dimensioned to comprise an expandable filter bed between said fluid inlet and said fluid outlet. A top collector is adapted for collecting substance filtered by said filter bed and top collector actuator is provided for actuation of the top collector. A top stratum position detector is constructed and adapted to detect a top stratum of the filter bed when in expanded state; and a controller is provided communicatively coupled to said top stratum position detector and said top collector actuator, for moving the top collector as a function of a detected top stratum position. A clean and automated way is provided to optimize the collection of filtered substance.

12 Claims, 7 Drawing Sheets

150

Figure 6
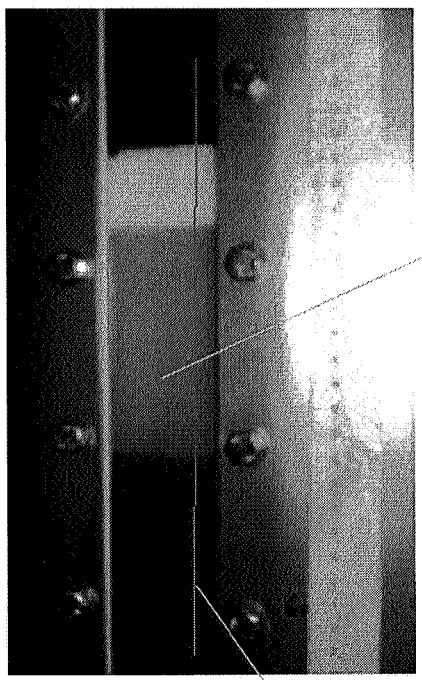
Figure 6A
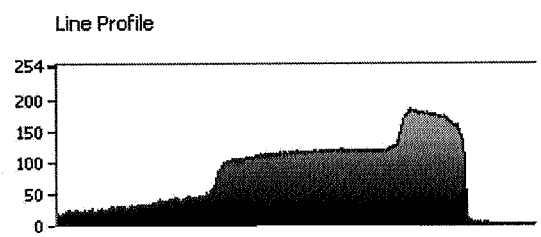
Figure 6B

US 7,927,487 B2

CHROMATOGRAPHIC COLUMN SYSTEM

This application is the U.S. National Phase of, and Applicant claims priority from, International Application Number PCT/NL2008/050170 filed 25 Mar. 2008 and European Patent Application No. 07104785.6 filed 23 Mar. 2007, each of which are incorporated herein by reference.

FIELD OF THE INVENTION

The invention regards a chromatographic column system, in particular, a chromatographic column system of the expanded bed adsorption type.

BACKGROUND OF THE INVENTION

In the art, expanded bed absorption (EBA) type chromatographic systems are an example of chromatographic separations where a filter bed can be movable, for example in a transition wherein the filter bed moves from a compressed to an expanded state. Indeed, where classical column chromatography uses a solid phase made by a packed bed, EBA typically uses a fluidized bed. Particles such as whole cells or cell debris, which would clog a packed bed column, readily pass through a fluidized bed. EBA can therefore be used on crude culture broths or slurries of broken cells. The feed flow rate is kept relatively low so that the solid packing remains stratified and does not fluidize completely. In the known expanded absorption type chromatographic systems the filtered substance is extracted by a top collector connected to the column's effluent port. However, in a situation where the filter bed is varied the quality of the filtered substance may be low, since the top collector will have a varying distance relative to the upper stratum of the filter bed, which may cause unwanted back mixing to take place. A chromatographic system of the above-identified type is described in U.S. Pat. No. 4,249,828

SUMMARY OF THE INVENTION

In one aspect, the invention provides a chromatographic column system comprising: a column connected to a fluid inlet and a fluid outlet and dimensioned to comprise an expandable filter bed between said fluid inlet and said fluid outlet; a top collector adapted for collecting substance filtered by said filter bed; and top collector actuator. A top stratum position detector is constructed and adapted to detect a top stratum of the filter bed when in expanded state; and a controller is provided communicatively coupled to said top stratum position detector and said top collector actuator, for moving the top collector as a function of a detected top stratum position. Accordingly, a clean and automated way can be provided to optimize the collection of filtered substance.

BRIEF DESCRIPTION OF THE DRAWINGS

FIG. 6 illustrates an image and image processing result to detect a top stratum.

DETAILED DESCRIPTION OF EMBODIMENTS

Figure 1:
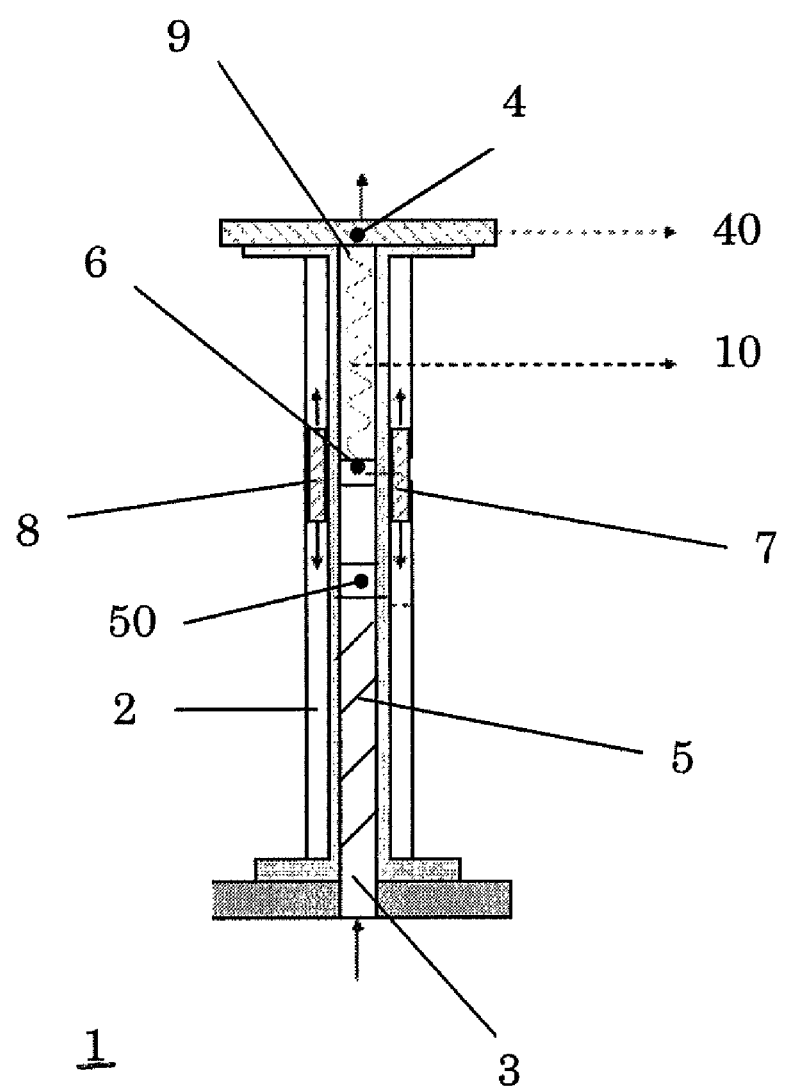
FIG. 1 illustrates a schematic side view of an embodiment according to the invention.

In FIG. 1 a schematic side view of an embodiment according to the invention is illustrated. The figure shows a chromatographic column system 1 comprising a column 2 connected to a fluid inlet 3 and a fluid outlet 4 provided in top plate 40. The column 2 is dimensioned to comprise an expandable filter bed 5 between said fluid inlet 3 and said fluid outlet 4. Typically the column is about one to three meters high and about 20 tot 200 centimeters wide. The expandable filter bed 5 provides filtering for a substance that is flowing to the fluid inlet 3 and is collected by a top collector 6 held in closed vicinity of a top layer or stratum 50 filter bed 5. Since the filter bed is kept in expanded state through a balance of fluid 3 flow and gravity exerting a gravity force on the filter 5 the top stratum 50 of the filter 5 is movable in axial direction along a column axis. The optimal filter quality is obtained just near the top stratum 50 of the filter bed 5 and to this end a top collector 6 is actuated by a top collector actuator 7.

Although other embodiments may be feasible were in the actuator 7 is internal of the column, in a preferred embodiment the top collector actuator is external of the column since this provide the most easy cleanable environment for the column 2. Although not specifically shown in FIG. 1 (see FIG. 3) a top stratum detector 8 is constructed to detect a top stratum 50 of the filter bed 5 when in expanded state. In this embodiment the detector 8 is integral to the actuator 7 but of course other embodiments are feasible where de top stratum position detector 8 is provided for example integral to a top collector 6 or as a separate piece.

Furthermore, separate from the detector 8 or connected thereto a controller 13 is provided, that is communicatively coupled to the top stratum position detector 8 and the top collector actuator 7 for moving the top collector 6 as a function of a detected top stratum position 50. The control can be provided in several ways, for example the top collector can be held at a predetermined distance between a top stratum 50 of the expanded filter bed 5 and the top collector 6, but this predetermined distance can also be a predetermined range. One advantageous aspect of this embodiment is the closed environment that is offered since the collector 6 is coupled to filtered substance outlet 9 provided in the top part of the column 2 via a coiled tubing 10 or flexible hose. The same detector 8, which in a preferred embodiment is non invasive of nature and based on optical signals, can also be used for detecting the liquid-air interface, to control the fluid flow 3.

Figure 2:
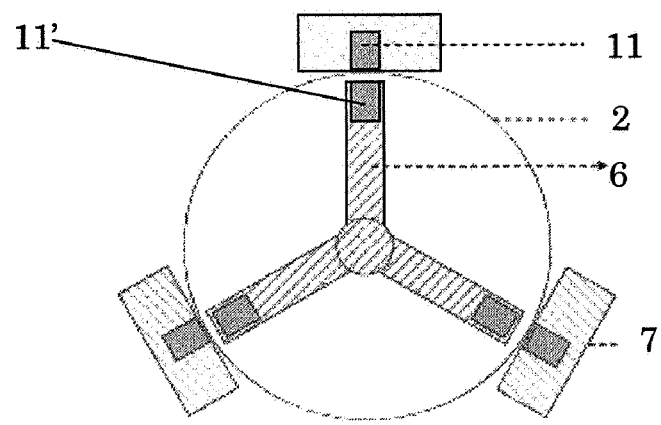
FIG. 2 illustrates a schematic top view of the embodiment of FIG. 1.

FIG. 2 illustrates a schematic top view of the embodiment of FIG. 1, in particular of top collector arrangement 60. It is shown that the column 2 comprises a collector actuator 7 that is arranged generally symmetric around a column axis. In the shown embodiment three pairs of complementary magnets 11, 11' are shown. The collector actuator 7 is arranged for axial movements along an axis of column 2, for example via linear magnets or wheels engaging on the outer wall of the column 2, The permanent magnets 11, 11' provide a magnetic coupling between the collector actuator 7 and the top collector 6 through the walls of the column 2. In particular when actuator 7 is axially moved the top collector 6 will follow due to magnetic coupling. To optimize the movement and minimize risk of blocking the magnetic elements are symmetrically arranged around a central axis of the column 2. This embodiment can be arranged in agreement with cGMP standards, for example, in FDA approved production using USP class VI materials, for pharmaceutical use etc.

Figure 3:
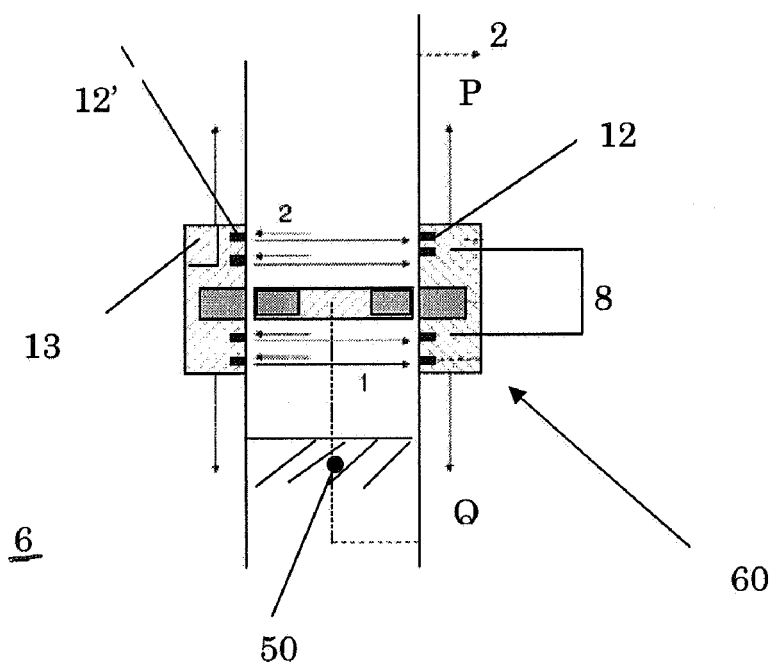
FIG. 3 illustrates a detailed schematic side view of a top collector element.

FIG. 3 illustrates a detailed schematic side view of a top collector arrangement 60. As explained with reference to FIG. 2 the top collector 6 is axially moveable along column 2 in directions P and Q. An array of sensors 8 is provided along length axis of the column 2. In the shown embodiment four pairs of sensors 12, 12' are provided; it is also possible to have more or less than four or for example two pairs of sensors 12, 12'. In this embodiment the sensors are optical sensors 12. The optical sensors are arranged to measure a transmission and/or a reflection, for example by a light-emitting element provided in or near the sensor 12'. Since in this embodiment the column 2 is of a transparent nature, the sensors 12 can be external of the column 2, improving the usability of the system 1. Although the shown embodiment uses optical sensors 12, it can be conceived that sensors of another nature, for instance acoustic sensors may be also feasible. By comparing a sensor signal in the upper part of the sensor array 8 and a sensor signal in the lower part, a gradient parameter can be calculated by a controller 13. In response to the measured parameter the controller provides actuation instructions to move the top collector. The movement is stopped when a maximum gradient value is detected or a gradient value is detected in the predetermined range. Accordingly optical sensors 12 are provided for measuring set gradient parameters as an optical parameter difference measured at opposite ends of the sensor array 8; indicative of a transition between a top filter stratum 50 and a (transparent) fluid above said stratum 50.

More in particular each pairs of sensors 12 comprises a light-emitting diode or laser emitter and a photo diode measuring incident light. The sensors 12 are arranged to measure a lateral reflection and transmission coefficient through the column 2. A ratio of light transmission and reflection is determined for each pair sensors 12. The ratio is compared and a gradient parameter is derived. Accordingly the position of the top collector 6 can be automatically adjusted following the expansion height of the filter bed 5 based on optical sensor measurements. In comparison with prior art this is an improvement since no manual positioning is needed. The control unit 13 is typically a PLC-control unit comprising a memory wherein the actions can be electronically stored.

Figure 4:
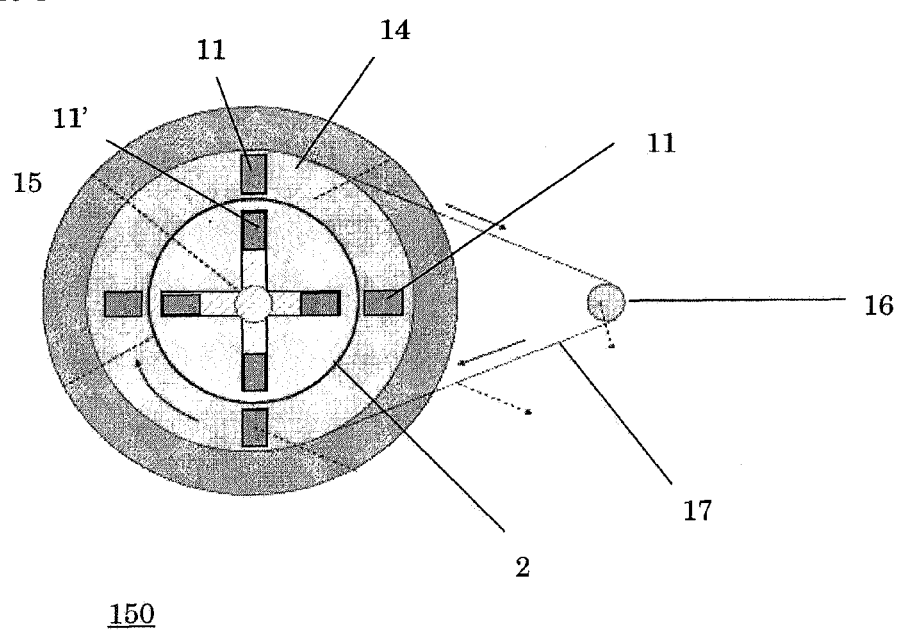
FIG. 4 illustrates a schematic axial view of a bottom distributor element.

FIG. 4 shows a bottom distributor arrangement 150, which can be another aspect of the present invention that can be used in addition or separate from the above described top collector arrangement 60 (FIG. 3). In particular it is shown that a moveable piece actuator 14 is movable external of the column 2 which actuator 14 comprises a magnetic element 11 as in FIG. 2. The magnetic element 11 is moveable external of the column so that a movable piece 15 provided in the column 2 is actuated by said moveable piece actuator 14. With this magnetic coupling instead of axial movement of the top collector 6 as shown in FIGS. 2 and 3, a rotary movement can be provided of the moveable piece 15, which is used as a bottom distributor element. In particular the bottom distributor 15 is actuated by bottom distributor actuator 14 arranged external of column 2. A motor 16 is provided and it drives belt 17 to rotate the actuator 14. Similar to the arrangement of FIG. 2 magnetic elements 11, 11' are provided to magnetically couple the bottom distributor 15 to the bottom distributor actuator 14. This arrangement has an advantage that a drive shaft is not necessary obviating the need for seals which is typically a maintenance problem and which is an environment where abrasive particles can harm the system. Since the drive system 16, 17 is arranged laterally of the column 2 the total of system height can be kept relatively low.

Figure 5:
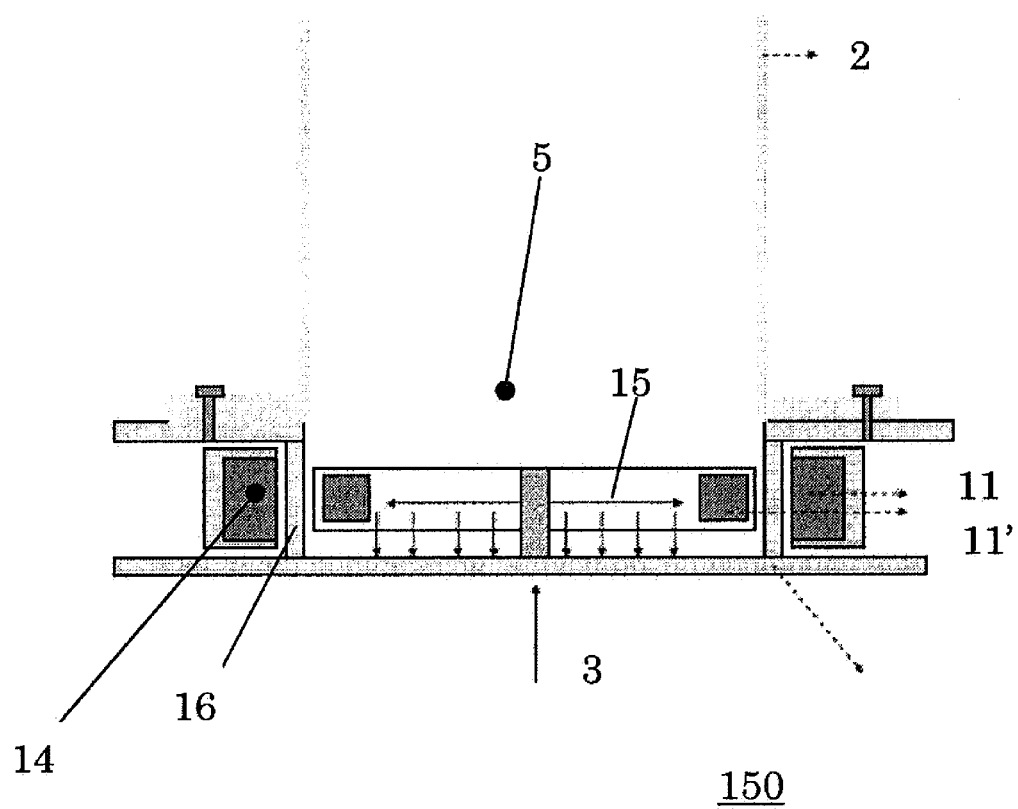
FIG. 5 illustrates a schematic side view of the bottom distributor element of FIG. 4.

FIG. 5 illustrates a schematic side view of the bottom distributor arrangement 150 shown in FIG. 4. In this arrangement typically the bottom distributor 15 is suspended by magnetic coupling in the lower part of column 2. In use the distributor element 15 will rotate slowly and intermittently clockwise and counter clockwise to keep the filter bed in a desired condition. However, on starting the filtering the filter bed will be compacted and the fluid flowing through fluid inlet 3 will be pressed through the filter bed 5. The distributor 15 can accelerate the expansion in an advantageous way. Through exerting a rotational movement of external actuator 14 the distributor 15 will be urged in rotational movements. When the filter bed is really compressed this will result in a considerable pressure exerted on the column wall. Therefore advantageously the lower end of the column 2 is provided with a reinforced side wall 16, typically of stainless steel or like. The filter bed distribution is enhanced since the rotary movement of the external distributor will provide a pulsating force when the distributor element 15 is not kept in magnetic coupling between elements 11 of 11'. The actuator will rotate to a next magnetic element 11' which will induce a pulsating force that enhances the filter bed 5 distribution and expansion. As already stated prior art systems typically suffer from presence of a rotary seal which is needed to seal a shaft. This seal will be negatively effected by the abrasive properties of absorbent particles. These arrangements are expensive in maintenance. The present embodiment is provided in a safe and reliable way without the need for seals. In addition a risk of column breach caused by pressure overload during start up is strongly reduced or eliminated due to the strong stainless steel housing at the columns bottom wherein the magnetic couple bottom distributor 15 is mounted. In addition, the torque provided by the external magnetic coupling, is less straining compared to a central rotation shaft arrangement.

Figure 7:
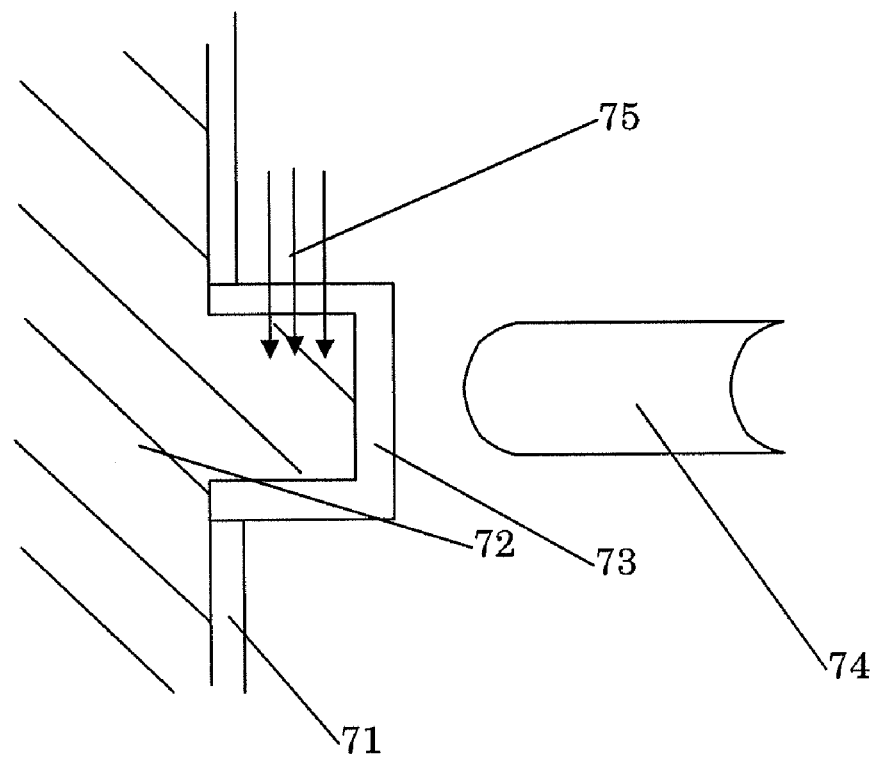
FIG. 7 schematically illustrates an image detector setup to detect a top stratum.

FIG. 6 illustrates an image (6A) and image processing result (6B) to detect a top stratum. Along line 60, an image parameter is detected, such as color value, or any other image parameter, including chrominance, luminance hue, or RGB-value. FIG. 6b illustrates that the changes in luminance of the black and white spectrum are indicative of the strata in the filter bed 5. As opposed to a movable sensor array as disclosed here above, direct image processing can be applied advantageously to interpret a larger surface area at once. In addition, the availability of (video) imaging makes processing more robust and can be assisted remotely by an operator, to accommodate different process situations. Accordingly, control of top collector position and effluent pump speed can be made more reliable while reducing wiring issues. FIG. 7 schematically illustrates an image detector setup to detect a top stratum. In this embodiment, the filter bed is illuminated by light coupled into the filter bed 72. In one exemplary embodiment, a measurement 'slit' or riser pipe 73 is provided as a transparent column part of the column wall 71. The riser pipe provides a recess, in which fluid 72 of the filter bed can be illuminated by light 75 coupled in laterally relative to the camera view, into the riser pipe 73, so that the image detector 74 can acquire a better-contrasted image. The image detector 74 can be fixed relative to the column or can be movable along with the actuator. The latter option provides a better contrast, in particular, with the illustrated illumination mode. Alternatively, a light source can be provided within the column, for example, as a part of the top collector 6 or as a transverse illumination through opposed transparent parts of the column wall.

Figure 8:
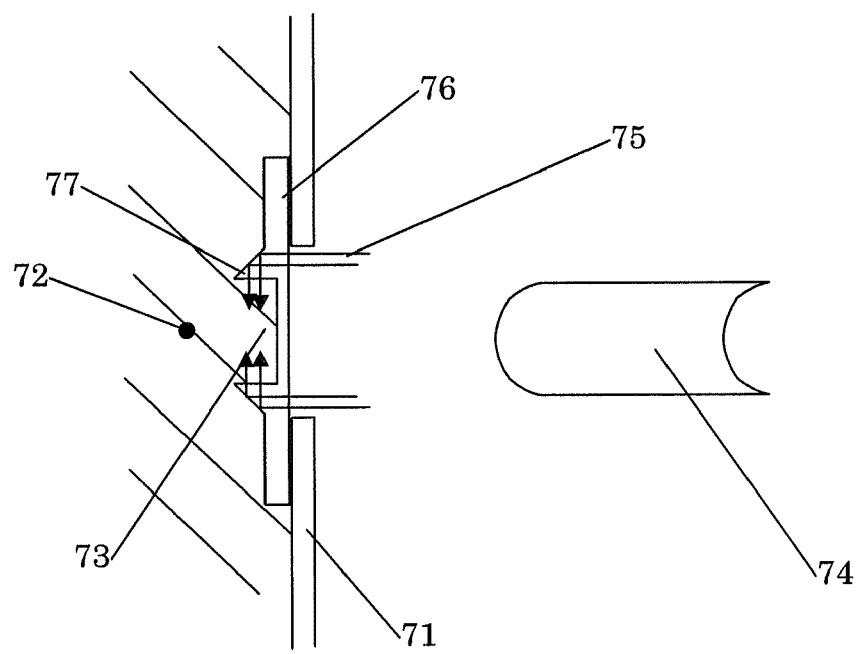
FIG. 8 schematically illustrates another image detector setup to detect a top stratum.

As another example, the recessed riser may be provided as a recess inwardly oriented to the column wall 71. FIG. 8 shows recessed transparent column part 76 having lateral sides arranged to reflect light into the recess via a prismatic end parts 77. Accordingly, an optical light guide is provided to project light 75 into the fluid 72, in order to illuminate the fluid close to the transparent column part 76.

While the invention has been illustrated and described in detail in the drawings and foregoing description, such illustration and description are to be considered illustrative or exemplary and not restrictive; the invention is not limited to the disclosed embodiments.

For example, the top collector actuator may be also arranged internal of column 2. In another example the top stratum detector is provided fixed to the column wall.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope. While in the embodiments, a top stratum of the resin bed is detected by the top stratum detector, other strata of interest may be likewise detected, for example, the interface between liquid air or liquid foam.

The invention claimed is:

1. Chromatographic column system comprising:
a column connected to a fluid inlet and a fluid outlet and dimensioned to comprise an expandable filter bed between said fluid inlet and said fluid outlet;
a top collector provided in said column adapted for collecting substance filtered by said filter bed;
top collector actuator;
a top stratum position detector is constructed and adapted to detect a top stratum position of the filter bed when in expanded state; and
a controller is provided communicatively coupled to said top stratum position detector and said top collector actuator, for moving the top collector as a function of a detected top stratum position, characterized in that said top collector actuator and said top stratum position detector are provided as a single top collector actuator piece that is translatable along said column and, the collector actuator being arranged external of said column for axial actuation of the collector piece; the collector actuator comprising a magnetic element; and wherein said collector piece comprises a complementary magnetic element so as to be magnetically coupled to said collector actuator.

2. A system according to claim 1, wherein said controller is arranged to maintain a distance between a top stratum of an expanded filter bed and said top collector in a predetermined range.

3. A system according to claim 1, wherein said top stratum position detector comprises a sensor array that is arranged along a length axis of the column; wherein the sensor array is arranged to measure a gradient parameter of said filter.

4. A system according to claim 3, wherein said gradient parameter is provided to said controller, which, in response, provides actuation instructions to move the top collector until a maximum gradient value is detected or a gradient value is detected in a predetermined range.

5. A system according to claim 3, wherein said sensor array comprises optical sensors for measuring said gradient parameter as an optical parameter difference measured at opposite ends of the sensor array; indicative of a transition between a top filter stratum and a fluid.

6. A system according to claim 5, wherein said optical sensors are arranged to measure a ratio of light transmission and reflection in a predetermined optical wavelength range.

7. A system according to claim 1, wherein said top stratum position detector is an optical detector and said column is of a transparent nature.

8. A system according to claim 1, wherein said column comprises a bottom distributor and a bottom distributor actuator external of said column arranged for rotational actuation of the bottom distributor; the bottom distributor actuator comprising a magnetic element; and wherein said bottom distributor comprises a complementary magnetic element so as to be magnetically coupled to said bottom distributor actuator.

9. A system according to claim 8, wherein said bottom distributor is magnetically suspended in a column part having a reinforced side wall.

10. A system according to claim 9, wherein said column is provided from a transparent material; and wherein said reinforced side wall is provided by stainless steel.

11. A system according to claim 1, wherein said magnetic elements comprise permanent magnets being symmetrically arranged around a central axis of the column.

12. A system according to claim 1, wherein a filtered substance outlet is provided in said column, and wherein said top collector is coupled to a filtered substance outlet via a coiled tubing or flexible hose.

* * * * *